United States Patent [19]

Arvinte

[11] Patent Number: 5,472,938
[45] Date of Patent: Dec. 5, 1995

[54] PHARMACEUTICAL DEPOT COMPOSITIONS CONTAINING HIRUDIN

[75] Inventor: Tudor Arvinte, Billinghurst, England

[73] Assignee: Ciba-Geigy Corporation, Ardsley, N.Y.

[21] Appl. No.: 199,506

[22] Filed: Feb. 17, 1994

[30] Foreign Application Priority Data

Feb. 18, 1993 [GB] United Kingdom ............... 9303275

[51] Int. Cl.$^6$ .................... A61K 38/17; A61K 47/02
[52] U.S. Cl. .................... 514/6; 514/12; 514/21; 514/769; 514/770; 514/822; 514/970
[58] Field of Search ............... 530/855, 324; 514/6, 12, 21, 970, 971, 769, 770, 822

[56] References Cited

U.S. PATENT DOCUMENTS

| | | | |
|---|---|---|---|
| 2,487,600 | 11/1949 | Schneiderwirth | 514/770 |
| 3,027,229 | 3/1962 | Towey et al. | 514/769 |
| 5,118,790 | 6/1992 | Winant et al. | 530/855 |
| 5,192,747 | 3/1993 | Krstenansky | 514/12 |
| 5,204,323 | 4/1993 | Findlay et al. | 530/383 |

FOREIGN PATENT DOCUMENTS

| | | |
|---|---|---|
| 0291982 | 11/1988 | European Pat. Off. . |
| 0525813 | 2/1993 | European Pat. Off. . |

*Primary Examiner*—Jeffrey E. Russel
*Attorney, Agent, or Firm*—Karen G. Kaiser

[57] ABSTRACT

The present invention relates to aqueous depot formulations of hirudin, particularly desulphatohirudin, which are very stable. These formulations contain water, hirudin, and calcium, magnesium, or zinc ions in the form of water insoluble salts, the salts being in a concentration of from 100 mM to 600 mM.

13 Claims, 4 Drawing Sheets

20mg/ml hirudin from 400mg/ml stock

PHARMACEUTICAL DEPOT COMPOSITIONS CONTAINING HIRUDIN

The present invention relates to aqueous formulations of hirudin and particularly to depot formulations.

$$\begin{array}{l}\text{Val Val Tyr Thr Asp Cys Thr Glu Ser Gly Gln Asn Leu Cys Leu Cys} \\ \text{1} \qquad\qquad\quad \text{5} \qquad\qquad\qquad\qquad \text{10} \qquad\qquad\qquad \text{15} \\[4pt] \text{Glu Gly Ser Asn Val Cys Gly Gln Gly Asn Xaa Cys Ile Leu Gly Ser} \\ \qquad\qquad\qquad \text{20} \qquad\qquad\qquad \text{25} \qquad\qquad\qquad \text{30} \\[4pt] \text{Asp Gly Glu Xaa Asn Gln Cys Val Thr Gly Glu Gly Thr Pro Xaa Pro} \\ \qquad\qquad\quad \text{35} \qquad\qquad\qquad \text{40} \qquad\qquad\qquad \text{45} \\[4pt] \text{Gln Ser Xaa Asn Asp Gly Asp Phe Glu Glu Ile Pro Glu Xaa} \\ \qquad\qquad \text{50} \qquad\qquad\qquad \text{55} \qquad\qquad\qquad \text{60} \end{array} \qquad (I)$$

Hirudin, an anticoagulant naturally occurring in leeches (*Hirudo medicinalis*), is not a single polypeptide species but a class of equally acting polypeptides consisting of at least four representatives designated hirudin variant 1 (HV1), hirudin variant 2 (HV2) (cf. European Patent Application No. 158 564) hirudin variant 3 (PA) [cf. PCT-Application No. 86/03493] and "des-(Val)$_2$-hirudin" (cf. European Patent Application No. 158 986). The variants differ in structure from each other by a number of amino acids (especially, the N-terminal sequence of HV1 is Val-Val-Tyr, that of HV2 and of HV3 is Ile-Thr-Tyr and that of "des-(Val)$_2$-hirudin" is Thr-Tyr) but have an accumulation of hydrophobic amino acids at the N-terminus and of polar amino acids at the C-terminus, a tyrosine residue (Tyr$^{63}$) present as sulphate monoester, three disulphide bridges and the anticoagulant activity in common.

In the past few years cDNAs and synthetic genes coding for hirudin variants have been cloned and expressed in microbial hosts. Although the expression products lack the sulphate monoester group at Tyr$^{63}$—and were therefore designated "desulphatohirudins" they turned out to exhibit approximately the same biological activity as the natural, sulphated hirudins. Desulphatohirudin variant HV1 has been expressed in *Escherichia coli* (European Patent Applications No. 158 564 and 168 342) and in *Saccharomyces cerevisiae* (European Patent Applications No. 168 342, 200 655, 225 633,252 854 and 341 215). Similarly, desulphatohirudin HV2 has been expressed in *Escherichia coli* (European Patent Applications No. 158 564) and in *Saccharomyces cerevisiae* (European Patent Application No. 200 655, PCT-Application No. 86/01224] and des-(Val)$_2$-desulphatohirudin has been expressed in *Escherichia coli* (European Patent Application No. 158 986).

According to the present invention, the term "hirudin" is intended to embrace hirudin, desulphathohirudin, a hirudin variant or a desulphatohirudin variant or a mutant thereof, respectively, described in the literature and in particular a desulphatohirudin compound or a mutant thereof obtainable from a transformed microorganism strain containing DNA which codes for a desulphatohirudin or a mutant thereof.- Such desulphatohirudins are, for example, desulphatohirudin variant HV1, HV1 modified (a, b), HV2, HV2 modified (a, b, c), HV3, variants of HV3 and des (Val$_2$)-desulphatohirudin.

Preferred desulphatohirudins are those having the formula (SEQ ID NO: 1)

in which a) Xaa at 27, 36 end 47 are each Lys, Xaa at 51 is His and Xaa at 62 is the peptide residue Glu-Tyr-Leu-Gin (HV1 ), or b) Xaa at 27 is Ile or Glu and Xaa at 36, 47, 51 and 62 are as defined in a) (HV1 modified a), or c) Xaa at 36 is Ile or Glu and Xaa at 27, 47, 51 and 62 are as defined in a) (HV1 modified a), or d) Xaa at 47 is Ile or Glu and Xaa at 27, 36, 51 and 62 are as defined in a) (HV1 modified a), or e) Xaa at 51 is Leu or Asp and Xaa at 27, 36, 47 and 62 are as defined in a) (HV1 modified a), or f) Xaa at 62 is selected from the group consisting of Glu-Tyr, Glu-Tyr-Leu, Glu-Asp-Leu-Gln, Glu-Glu-Leu-Gln, Glu-Tyr-Lys-Arg, Glu-Asp-Lys-Arg, Glu-Lys-Leu-Gln, Ser-Phe-Arg-Tyr, Trp-Glu-Leu-Arg, Glu-Tyr-Leu-Gln-Pro and Glu-Tyr-Leu-Gln-Arg and Xaa at 27, 36, 47 and 51 are as defined in a) (HV1 modified b), or having the formula (SEQ ID NO: 2)

```
Leu Thr Tyr Thr Asp Cys Thr Glu Ser Gly Gln Asn Leu Cys Leu Cys         (II)
1              5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
            35                  40                  45

Gln Ser His Asn Asp Gly Asp Phe Glu Glu Ile Pro Glu Glu Tyr Leu
        50                  55                  60

Gln
65
``` or having the formula (SEQ ID NO: 3)

```
Ile Thr Tyr Thr Asp Cys Thr Glu Ser Gly Gln Asn Leu Cys Leu Cys         (III)
1              5                   10                  15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Xaa Pro
            35                  40                  45

Glu Ser His Asn Asn Gly Asp Phe Glu Glu Ile Pro Glu Glu Xaa Leu
        50                  55                  60

Gln
65
``` in which
    a) Xaa at 47 is Asn and Xaa at 63 is Tyr HV2), or
    b) Xaa at 47 is Lys, Arg or His and Xaa at 63 is Tyr (HV2 modified a), or
    c) Xaa at 63 is Glu or Asp and Xaa at 47 is Asn (HV2 modified b), or having the formula (SEQ ID NO: 4)

```
Val Val Tyr Thr Asp Cys Thr Glu Ser Gly Gln Asn Leu Cys Leu Cys         (IV)
1              5                   10                  15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Asn Pro
            35                  40                  45

Glu Ser His Asn Asn Gly Asp Phe Glu Glu Ile Pro Glu Glu Tyr Leu
        50                  55                  60

Gln
65
``` or having the formula (SEQ ID NO: 5)

```
Ile Thr Tyr Thr Asp Cys Thr Glu Ser Gly Gln Asn Leu Cys Leu Cys         (V)
1              5                   10                  15

Glu Gly Ser Asn Val Cys Gly Lys Gly Asn Lys Cys Ile Leu Gly Ser
            20                  25                  30

Gln Gly Lys Asp Asn Gln Cys Val Thr Gly Glu Gly Thr Pro Lys Pro
            35                  40                  45
```

-continued

```
Gln Ser His Asn Gln Gly Asp Phe Gly Pro Ile Pro Gly Asp Ala Tyr
 50                      55                  60

Asp Glu
 65
```

HV3 and variants of said HV3 which are characterised by a shortening of the primary structure by 1 or 2 amino acids at the N-terminus or by 18, 10, 9, 6, 4 or 2 amino acids at the C-terminus.

Particularly preferred desulphatohirudin compounds are those of formula I in which the Xaa groups are as defined under a) or the compound of formula III in which Xaa at 47 is Lys and Xaa at 63 is Tyr.

The most preferred hirudin is desulfatohirudin HV1 having the formula I in which Xaa at 27, 36 and 47 are each Lys, Xaa at 51 is His and Xaa at 62 is the peptide residue Glu-Tyr-Leu-Gln.

The hirudins used in the present invention can be prepared synthetically, e.g. chemically or preferably by recombinant techniques, or by isolation from leeches.

According to the present invention the term "mutant" refers to proteins (muteins) exhibiting antithrombotic activity which differ from native hirudin or desulphathohirudin by simple or multiple mutations (cf. European Patent Applications No. 352 227 and No. 352 228). The DNA coding for said mutants which can be prepared by methods known in the art e.g. site-directed mutagensis, is cloned and expressed in microbial hosts such as *Escherichia coli* and *Saccharomyces cerevisiae*.

The hirudin compounds used in the invention can be in the free form but also in the form of their salts. As they contain free amino groups in several amino acid residues, the compounds can be in the form of acid addition salts. Suitable acid addition salts are in particular pharmacologically acceptable salts with conventional therapeutically acceptable acids. Representative inorganic acids are hydrohalic acids (such as hydrochloric acid), and also sulfuric acid, phosphoric acid and pyrophosphoric acid. Representative organic acids are in particular arenesulfonic acids (such as benzenesulfonic or p-toluenesulfonic acid), or lower alkanesulfonic acids (such as methanesulfonic acid), as well as carboxylic acids such as acetic acid, lactic acid, palmitic acid, stearic acid, malic acid, tartaric acid, ascorbic acid and citric acid. As, however, the compound used in the invention also contain free carboxyl groups in several amino acid residues, which carboxyl groups impart acidic character to the entire peptide, they can also be in the form of salts with inorganic or organic bases, e.g. sodium, potassium, calcium or magnesium salts, or also ammonium salts derived from ammonia or a pharmacologically acceptable organic nitrogen-containing base. However, as they contain at the same time free carboxyl groups and free amino groups, they can also be in the form of inner salts. Pharmacologically acceptable salts are preferred.

One problem in developing a dosage form containing hirudin is its poor stability in aqueous solutions. This is a major obstacle in the development of a prefilled syringe formulation, a dosage form having advantages such as being more user friendly for patients and having reduced production costs.

The poor stability can be seen when hirudin is analysed by chromatographic methods.

MONO Q METHOD: The stability of hirudin can be analysed by FPLC (fine protein liquid chromatography) using a Mono-Q column (10 μm particle size, 5.0×50 mm, purchased from Pharmacia). The method was developed by Ciba-Geigy, Basel. Solvent A is 50 mM $HCOONH_4$ in $H_2O$ pH 4.5, and solvent B is 50 mM $HCOONH_4$ in $H_2O$, pH 3.5. The elution is performed at room temperature (22° C.) using a flow rate of 1.4 ml/min. The binary elution for the first 5 min is at constant flow of 20% B, followed by a linear gradient from 20% B to 75% B over 10 minutes, and 2 minutes at 100% B after which the column is equilibrated for 2 min at the starting conditions of 20% B.

PROPAC METHOD: A recently published method for hirudin analysis can also be used [Tuong, A., Maftouh, M., Ponthus, C., Whitechurch, O., Roitsch, C., and Picard, C. (1992) "Characterisation of the Deamidated Forms of Recombinant Hirudin" Biochemistry 31, 8291–8299]. In this method a ProPac PAl anion-exchange column (250×4 mm i.d.) from Dionex is used. Solvent A is 20 mM Tris-HCl, pH 7.0 and solvent B is 0.5M NaCL in A. Isocrastic elution for 5 min at 28% is followed by a linear gradient from 28%B to 54%B over 60 min at a flow rate of 1.3 ml/mim.

Typical chromatograms of recombinant hirudin (CGP 39393) in water (20 mg/ml hirudin) using the Mono Q and ProPac methods are shown in FIG. 1. As can be seen the methods produce similar results.

The two peaks which elute in the front of the main peak (FIG. 1) are referred to as Q4 and Q5 peaks, respectively. FIG. 2 shows that storage of hirudin in water results in an increase of the Q4 and Q5 peaks with time and also the occurrence of peaks behind the main hirudin peak. The exact nature of the products which produce those extra peaks is not known.

For the use of hirudin in different indications, for example in the prevention of deep vein thrombosis it would be advantageous to present the hirudin as a depot formulation. Such formulations could allow for a once daily application, reducing the problems of patient compliance.

We have now found that depot formulations can be made using calcium, magnesium or zinc ions. These formulations slowly release hirudin and also have long term chemical stability.

Accordingly, the present invention provides an aqueous depot formulation comprising water, hirudin and calcium, magnesium or zinc ions in the form of a water insoluble salt.

The water insoluble salt is preferably a phosphate as they are very insoluble.

The depot formulation may have pH of from 4 to 11, preferably from 5 to 9.

The concentration of the metal salt may be from 100 mM to 600 mM, preferably from 100 mM to 300 mM and most preferably about 150 mM. If the concentration is higher than a usable physiological concentration, the depot may be diluted to a physiological concentration before use.

The concentration of hirudin may be from 1 to 600 mg/ml, preferably from 20 to 80 mg/ml. If a high concentration is present it may be diluted, e.g. to the 20 to 80 mg/ml range before use.

The particle size of the water insoluble salt may be from 10 to 30 μm diameter, preferably from 10 to 20 μm diameter.

The depot formulation may be prepared by precipitating the water insoluble salt in situ in an aqueous hirudin solution. For example the chloride of the chosen metal (Ca, Mg or Zn) may be mixed with an alkali metal phosphate. The pH of the resulting formulation may then be adjusted using e.g. hydrochloric acid or sodium hydroxide as appropriate.

After precipitation the depot formulation has a milky appearance and sedimented in time. However, after shaking, the formulation becomes milky again.

The preferred metal for the depot in zinc.

The formulations of the invention may also contain a sugar such as sucrose, trehalose or, preferably, mannitol.

The hirudin which is present in the depot formulations is very pure and is stable over a long period of time, at least for several months. The formulations may be stored at room temperature or below, e.g. at 4°. They are stable for longer periods at lower temperatures. Formulations have been stored at room temperature for at least 3 months and have shown no degradation.

The formulations of the invention may be administered parenterally by injection or subcutaneously. It has been found that when hirudin is administered as a depot formulation according to the invention, there is less bleeding around the injection site than when it is administered as a simple solution.

Figure 1A:
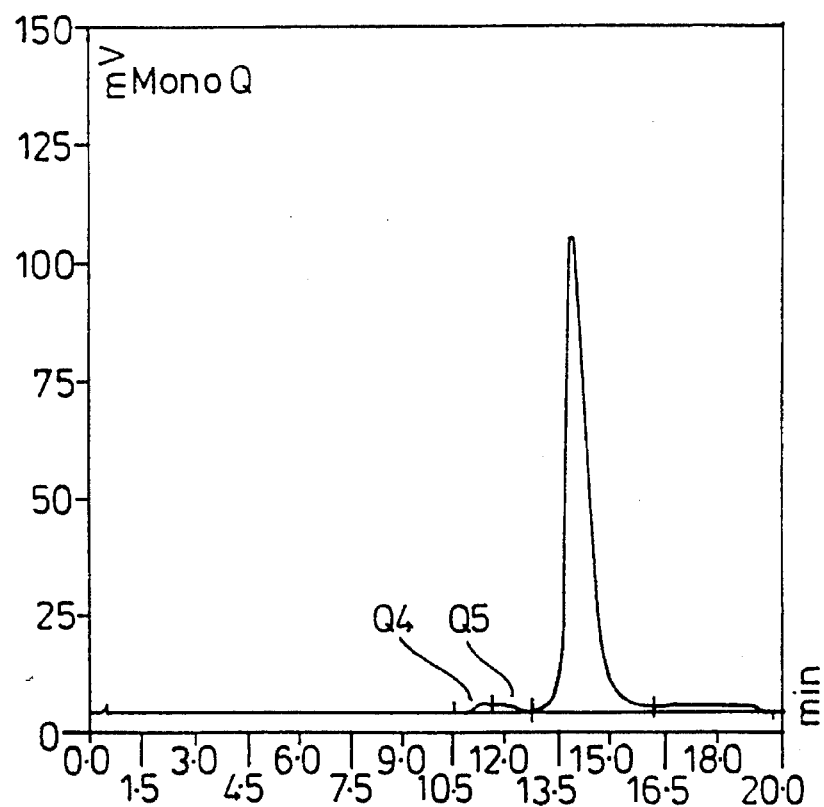
FIG. 1a and 1b depicts a chromatogram of recombinant hirudin (CGP 39393) in water (20 mg/ml hirudin) using the Mono Q and ProPac methods.
Figure 1B:
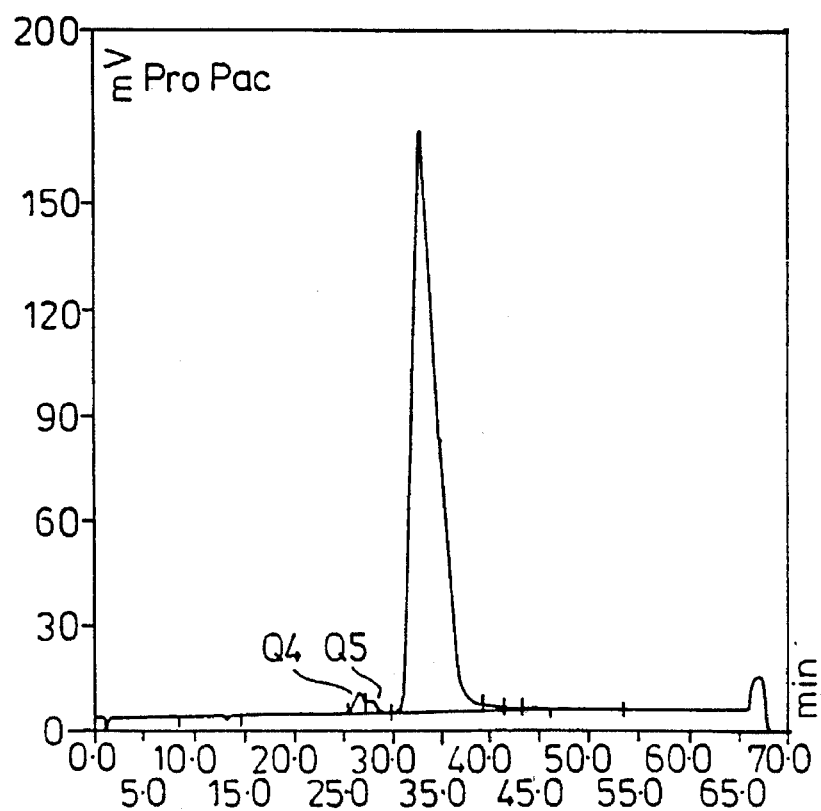
Figure 2A:
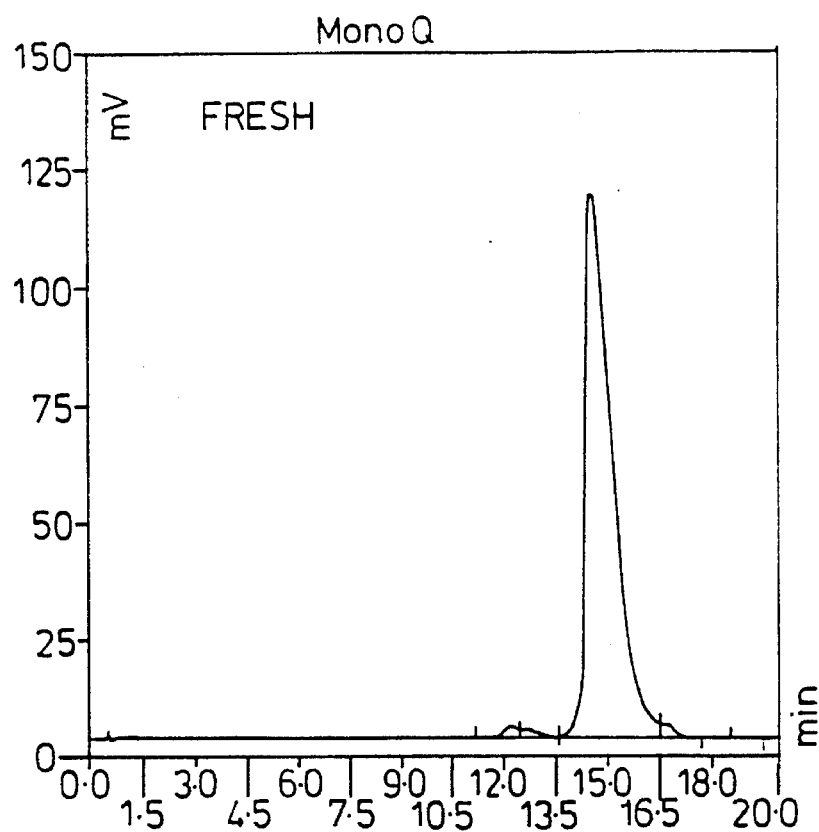
FIG. 2a and 2b depicts the storage of hirudin in water which results in an increase of the Q4 and Q5 peaks with time and the occurrence of peaks behind the main hirudin peak.
Figure 2B:
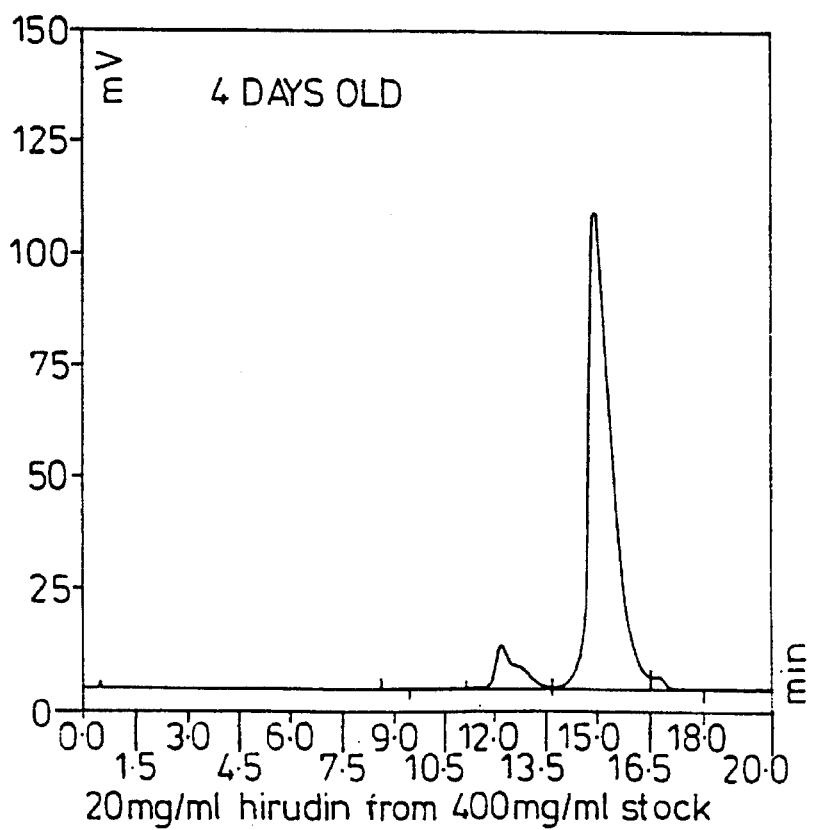

The invention is illustrated by the following Examples.

EXAMPLE 1

Solution A contains 2.43M $ZnCl_2$, and 0.455M $Na_2HPO_4$ in water at pH2.5, pH adjusted with HCl. Solution B consists of 0.6 M NaOH, 0.25M NaCl. A Solution C is made by mixing 2 parts of a stock solution of hirudin in water (80 mg/ml) with 1.05 parts of Solution A [ratio 2:1.05 (v/v)]. The depot formulation is obtained by mixing water, Solution B, and Solution C in the weight ratio of 0.66:0.183:0.4, respectively.

Similar mixtures are made using $CaCl_2$ or $MgCl_2$ instead of $ZnCl_2$.

EXAMPLE 2

The depot formulations obtained in Example 1 are centrifuged. The supernatant is removed and analysed and water added to the residue. It is found that after the first centrifuge 85–95% of the hirudin is in the pellet formed.

This is then shaken and centrifuged and the process repeated again.

Table 1 shows the Mono Q analysis of the supernatant of depot formulations after first, second and third centrifugation:

TABLE 1

| DEPOT FORMULATION | % AREA MAIN PEAK MONO Q METHOD |
| --- | --- |
| 20 mg/ml Zn | 99.7 |
| 20 mg/ml Mg | 99.7 |
| 20 mg/ml Ca | 98.6 |
| First supernatant | |
| Zn | 96.6 |
| Mg | 99.5 |
| Ca | 99.7 |
| Second supernatant | |
| Zn | 98.7 |
| Mg | 99.9 |
| Ca | 100 |
| Third supernatant | |
| Zn | 100 |
| Mg | 100 |
| Ca | 100 |

Samples were 150 mM pH 7.4

The data in Table 1 show that the supernatants contain very pure hirudin. The relative amount of hirudin after each centrifugation is reducing, data not shown. The data in Table 1 also shows that each formulation acts as a depot: after each centrifugation the addition of water over the residue results in more hirudin release.

EXAMPLE 3

Depot formulations made by the process of Example 1 are stored for 5 months at 4° C. and then the hirudin is analysed using the ProPac Method. The results are given in Table II.

TABLE II

| ProPac analysis of 5 months old depot formulations | |
| --- | --- |
| DEPOT | % AREA MAIN PEAK PROPAC METHOD |
| Zn, pH7 | 97 |
| Ca, pH6 | 92 |
| Mg, pH6 | 92 |
| Mg, pH7 | 88 |
| Zn, pH8.5 | 70 |
| Zn, pH5 | 88 |

The Zn and Ca depot formulations from Table II in the pH range 6–7 showed no undue instability by the ProPac method. The Zn formulation at pH 8.5 showed some instability.

EXAMPLE 4

Solution A1 contains 165 mM Zn $Cl_2$, 2.11 mM $Na_2HPO_4$ and 37.8 mM HCl. Solution B1 contains 0.6N NaOH. Hirudin powder is added to 31.7 parts by volume solution A1, followed by 55 parts by volume mannitol solution, 198 mM and then 13.3 parts by volume solution B1. The solution becomes turbid as the depot is formed. Hirudin is used in an amount of 20 mg/ml water used. No pH adjustment is needed.

EXAMPLE 5

Hirudin is dissolved in 13.5 parts by volume of a mannitol solution, 198 mM and 27.75 parts by volume water. To this is added 10 parts by volume solution B1 (see Example 4) and then 23.75 parts by volume solution A1 (see Example 4). The solution becomes turbid as the depot is formed. Hirudin is used in an amount of 20 mg/ml water used. No pH adjustment is needed.

EXAMPLE 6

Hirudin is dissolved in 1 part by volume CaCl$_2$ solution, 120 mM and then 1 part by volume K$_2$HPO$_4$ solution, 150 mM. The solution becomes turbid as the depot is formed. Hirudin is used in an amount of 20 mg/ml of water used. The pH is adjusted to 7.4 by the addition of 1M NaOH solution.

EXAMPLE 7

In order to illustrate the depot effect, hirudin is administered subcutaneously to rats (n=6) either as a saline solution (hir/sal) or in a zinc depot formulation (Zn/hir).

Figure 3:
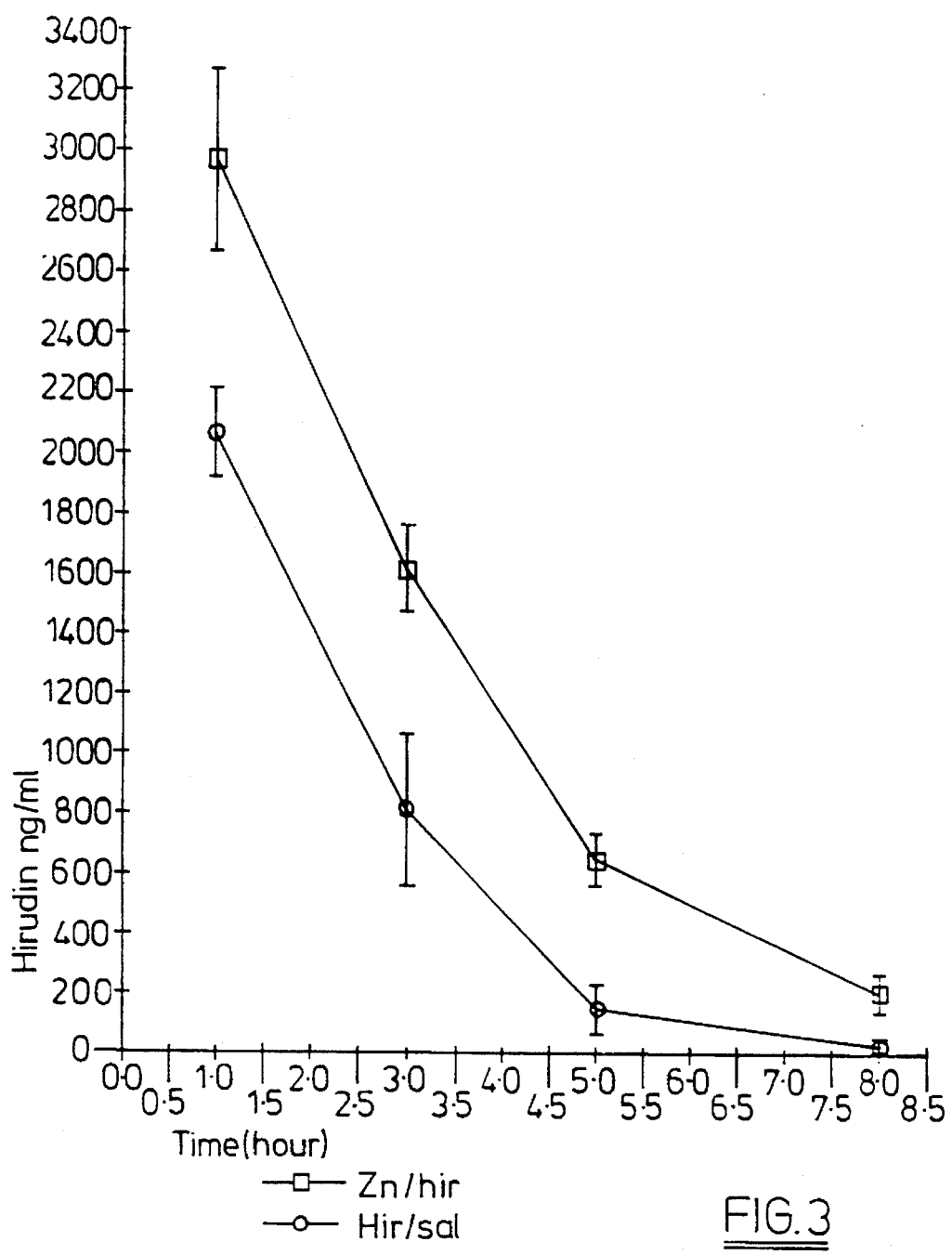
FIG. 3 depicts the concentration of hirudin in rat plasma of Example 7, infra, as measured at 1, 3, 5, and 8 hours after administration as assayed by sandwich ELISA.

The concentration of hirudin in plasma from the rats is measured at 1, 3, 5 and 8 hours after administration. Heparinised plasma is assayed by sandwich ELISA. The results are shown in FIG. 3.

Figure 4:
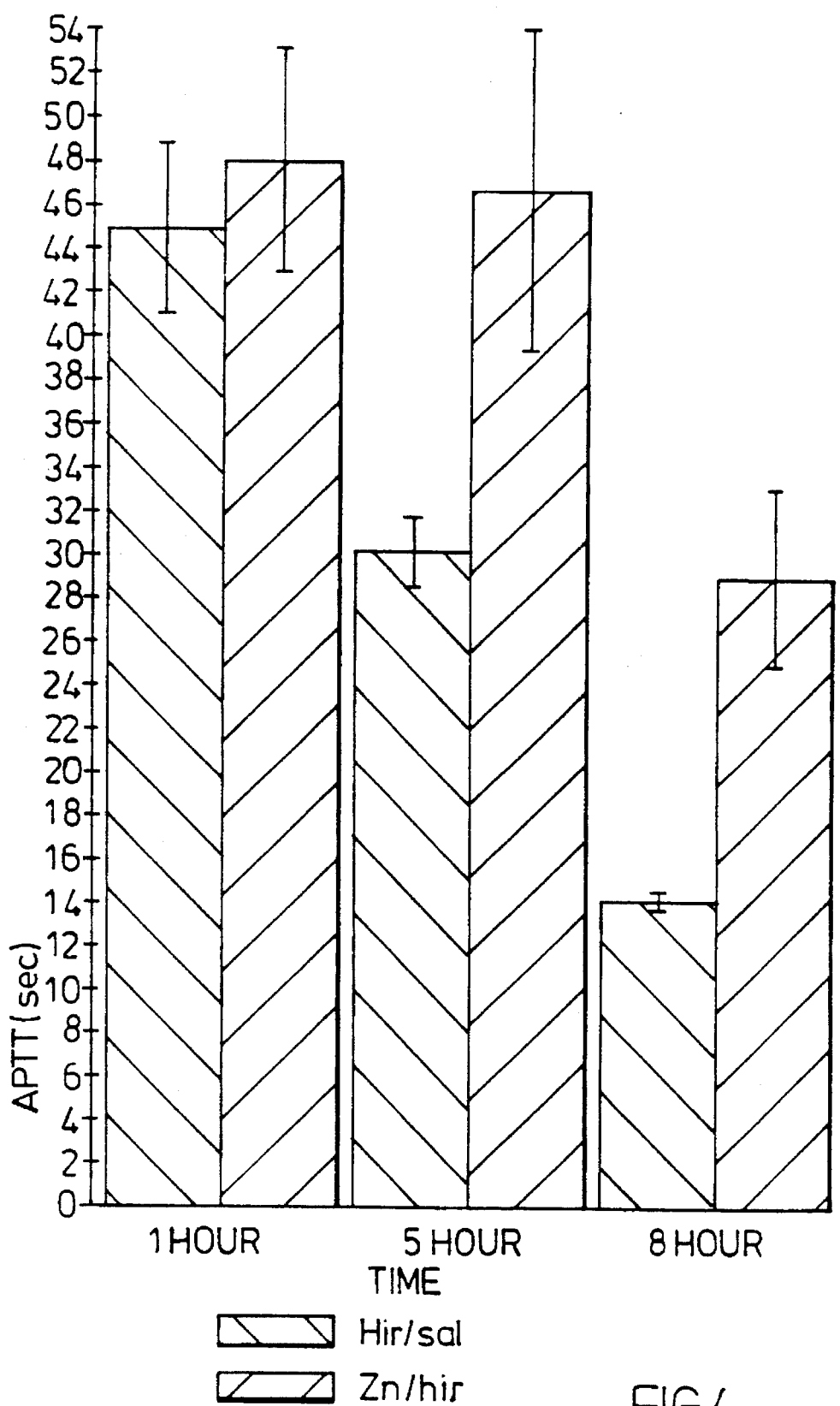
FIG. 4 depicts the activated particle thromboplastin time of Example 7, infra, measured at 1, 5, and 8 hours after administration.

The Activiated particle thromboplastin time (APTT) is measured at 1, 5 and 8 hours after administration. The results are shown in FIG. 4.

The depot effect is shown by the longer lasting action of the hirudin.

---

I claim:

1. An aqueous depot formulation comprising water, hirudin, and metal ions in the form of a water insoluble salt in which the metal is selected from calcium, magnesium, and zinc, the concentration of said salt being from 100 mM to 600 mM.

2. A formulation as claimed in claim 1 in which the water insoluble salt is a phosphate.

3. A formulation as claimed in claim 1 which has a pH of from 4 to 11.

4. A formulation as claimed in claim 3 which has a pH of from 6 to 8.

5. A formulation as claimed in claim 1 in which the concentration of metal salt is about 150 mM.

6. A formulation as claimed in claim 1 in which the concentration of hirudin is from 1 to 600 mg/ml.

7. A formulation as claimed in claim 6 in which the concentration of hirudin is from 20 to 80 mg/ml.

8. A formulation as claimed in claim 1 in which the hirudin is a desulphatohirudin variant or a mutant thereof.

9. A formulation as claimed in claim 1 in which the hirudin is desulphatohirudin HV1.

10. A formulation as claimed in claim 1 in which the particle size of the water insoluble salt is from 10 to 30 μm diameter.

11. A formulation as claimed in claim 1 in which the particle size of the water insoluble salt is from 10 to 20 μm diameter.

12. A formulation as claimed in claim 1 which also contains a sugar.

13. A formulation as claimed in claim 12 in which the sugar is mannitol.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:1:

```
Val  Val  Tyr  Thr  Asp  Cys  Thr  Glu  Ser  Gly  Gln  Asn  Leu  Cys  Leu  Cys
 1              5                            10                       15

Glu  Gly  Ser  Asn  Val  Cys  Gly  Gln  Gly  Asn  Xaa  Cys  Ile  Leu  Gly  Ser
              20                            25                       30

Asp  Gly  Glu  Xaa  Asn  Gln  Cys  Val  Thr  Gly  Glu  Gly  Thr  Pro  Xaa  Pro
              35                       40                       45

Gln  Ser  Xaa  Asn  Asp  Gly  Asp  Phe  Glu  Glu  Ile  Pro  Glu  Xaa
              50                       55                  60
```

( 2 ) INFORMATION FOR SEQ ID NO:2:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Leu  Thr  Tyr  Thr  Asp  Cys  Thr  Glu  Ser  Gly  Gln  Asn  Leu  Cys  Leu  Cys
 1              5                            10                       15

Glu  Gly  Ser  Asn  Val  Cys  Gly  Gln  Gly  Asn  Lys  Cys  Ile  Leu  Gly  Ser
              20                            25                       30
```

```
         Asp  Gly  Glu  Lys  Asn  Gln  Cys  Val  Thr  Gly  Glu  Gly  Thr  Pro  Lys  Pro
                   35                  40                       45

Gln  Ser  His  Asn  Asp  Gly  Asp  Phe  Glu  Glu  Ile  Pro  Glu  Glu  Tyr  Leu
                   50                  55                       60

Gln
         65
```

( 2 ) INFORMATION FOR SEQ ID NO:3:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:3:

```
         Ile  Thr  Tyr  Thr  Asp  Cys  Thr  Glu  Ser  Gly  Gln  Asn  Leu  Cys  Leu  Cys
         1                   5                       10                      15

Glu  Gly  Ser  Asn  Val  Cys  Gly  Lys  Gly  Asn  Lys  Cys  Ile  Leu  Gly  Ser
                        20                       25                      30

Asn  Gly  Lys  Gly  Asn  Gln  Cys  Val  Thr  Gly  Glu  Gly  Thr  Pro  Xaa  Pro
                   35                  40                       45

Glu  Ser  His  Asn  Asn  Gly  Asp  Phe  Glu  Glu  Ile  Pro  Glu  Glu  Xaa  Leu
                   50                  55                       60

Gln
         65
```

( 2 ) INFORMATION FOR SEQ ID NO:4:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:4:

```
         Val  Val  Tyr  Thr  Asp  Cys  Thr  Glu  Ser  Gly  Gln  Asn  Leu  Cys  Leu  Cys
         1                   5                       10                      15

Glu  Gly  Ser  Asn  Val  Cys  Gly  Lys  Gly  Asn  Lys  Cys  Ile  Leu  Gly  Ser
                        20                       25                      30

Asn  Gly  Lys  Gly  Asn  Gln  Cys  Val  Thr  Gly  Glu  Gly  Thr  Pro  Asn  Pro
                   35                  40                       45

Glu  Ser  His  Asn  Asn  Gly  Asp  Phe  Glu  Glu  Ile  Pro  Glu  Glu  Tyr  Leu
                   50                  55                       60

Gln
         65
```

( 2 ) INFORMATION FOR SEQ ID NO:5:

( i ) SEQUENCE CHARACTERISTICS:
        ( A ) LENGTH: 66 amino acids (B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:5:

```
Ile Thr Tyr Thr Asp Cys Thr Glu Ser Gly Gln Asn Leu Cys Leu Cys
 1               5                  10                  15
Glu Gly Ser Asn Val Cys Gly Lys Gly Asn Lys Cys Ile Leu Gly Ser
            20                  25                  30
Gln Gly Lys Asp Asn Gln Cys Val Thr Gly Glu Gly Thr Pro Lys Pro
        35                  40                  45
Gln Ser His Asn Gln Gly Asp Phe Glu Pro Ile Pro Glu Asp Ala Tyr
    50                  55                  60
Asp Glu
65
```